US00PP33612P2

(12) United States Plant Patent
Hansen

(10) Patent No.: US PP33,612 P2
(45) Date of Patent: Nov. 2, 2021

(54) ASTER PLANT NAMED 'GRAPE CRUSH'

(50) Latin Name: *Symphyotrichum novae-angliae*
Varietal Denomination: Grape Crush

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,043

(22) Filed: Feb. 23, 2021

(51) Int. Cl.
*A01H 5/02* (2018.01)
*A01H 6/14* (2018.01)

(52) U.S. Cl.
USPC ..... Plt./355

(58) Field of Classification Search
USPC ..... Plt./355
CPC ... A01H 5/02; A01H 5/00; A01H 6/14; A01H 6/1408; A01H 6/30
See application file for complete search history.

(56) References Cited

PUBLICATIONS

Leo Berbee Young Plants Emerald Coast Growers Pricing 2020-2021, retrieved on May 17, 2021, retrieved from the Internet at https://www.berbeeyoungplants.com/plants/ECG%202021.pdf, pp. 1, 8. (Year: 2021).*

Shaw, The splitting of Aster 2014, retrieved on May 17, 2021, retrieved from the Internet at https://www.rhs.org.uk/about-the-rhs/publications/the-plant-review/2014-issues/june/the-splitting-of-aster.pdf, 120-125. (Year: 2014).*

* cited by examiner

*Primary Examiner* — June Hwu

(57) ABSTRACT

A new and distinct Aster plant named 'Grape Crush', with heavily-branched, very rounded mound habit, dark green, lanceolate foliage and large semi-double inflorescences with numerous, overlapping, dark purple florets beginning in late August and continuing for about six weeks. The new plant is useful for landscaping, as a specimen or en masse and as a cut flower.

1 Drawing Sheet

Botanical designation: *Symphyotrichum novae-angliae*.
Cultivar denomination: 'Grape Crush'.

STATEMENT REGARDING PRIOR DISCLOSURES UNDER 37 CFR 1.77(b)(6)

The first public disclosure of the claimed plant, in the form of a sale, was made by Walters Gardens, Inc. on Sep. 16, 2020. Prior to that, on Feb. 1, 2020 the claimed plant was displayed as a photograph with a brief non-enabling description on a website operated by Walters Gardens, Inc., followed by listing with a photograph and brief description in the Walters Gardens 19-20 Catalog circulated on May 20, 2020. Walters Gardens, Inc. obtained the plant and all information relating thereto, from the inventor. No plants of Aster 'Grape Crush' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct Aster herein also referred to as Aster 'Grape Crush', by the cultivar name, 'Grape Crush', or as the new plant. The new plant was selected by the inventor as a single seedling resulting from a self-pollination of a proprietary, unreleased, unnamed seedling known only by the breeder code 13-4-1 (not patented) in a research facility of a wholesale perennial grower based in Zeeland, Mich., USA. The cross was performed on Jul. 7, 2015 and the seeds from this cross were collected in the fall of 2015. The single seedling was then isolated and compared in subsequent years to other Aster and subsequently found to be different from all cultivars known to the discoverer and eventually given the breeder code 15-2-4.

Asexual propagation at the same nursery in Zeeland, Mich., USA by basal shoot tip cuttings since October of 2017 has shown 'Grape Crush' to be stable and reproduce true to type in successive generations.

SUMMARY OF THE PLANT

Aster 'Grape Crush' has not been observed in all possible environmental conditions. The phenotype may vary slightly with changes in environments such as light intensity, fertility, water availability, etc. without, however any variation in genotype.

Aster 'Grape Crush' is distinct from all cultivars known to the inventor in the following traits:

1. Compact, very rounded mound of about 40 cm tall and 52 cm wide;
2. Dark green lanceolate foliage;
3. Heavily-branched peduncles with densely-packed inflorescences;
4. Inflorescences with multiple rows of overlapping dark purple ray florets;
5. Long flowering period beginning early fall and continuing for about six weeks;

Plants of Aster 'Grape Crush' are most similar to 'Purple Dome' (not patented), 'X Blue' U.S. Plant Pat. No. 29,109 and 'Billowing Violet' U.S. Plant Pat. 32,557. 'Purple Dome' is larger in habit, both taller and broader than the new plant, and the more numerous ray florets are more pale-purple. 'Billowing Violet' has fewer and slightly smaller ray petals per inflorescence, is taller in habit, and the ray floret color is light purple. 'X Blue' has slightly smaller and slightly fewer ray florets per inflorescence, and the ray florets are strong to light purple.

The parent plant, 13-4-1, has a taller habit and the flower color not as dark.

BRIEF DESCRIPTION OF THE DRAWINGS

The color drawings illustrate the overall characteristics of Aster 'Grape Crush' as a two-year-old plant in a full-sun trial garden in Zeeland, Mich. The colors are as true as reasonably possible given the technology available. The color values may vary slightly depending on light intensity and quality.

DETAILED BOTANICAL DESCRIPTION

Figure 1:
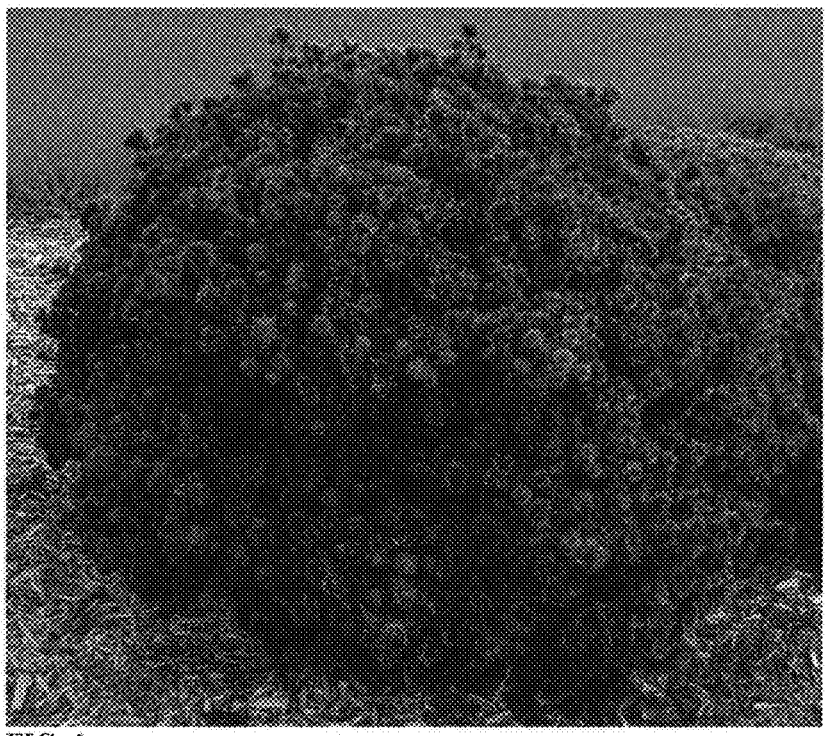
FIG. 1 shows the new plant in a trial facility.
Figure 2:
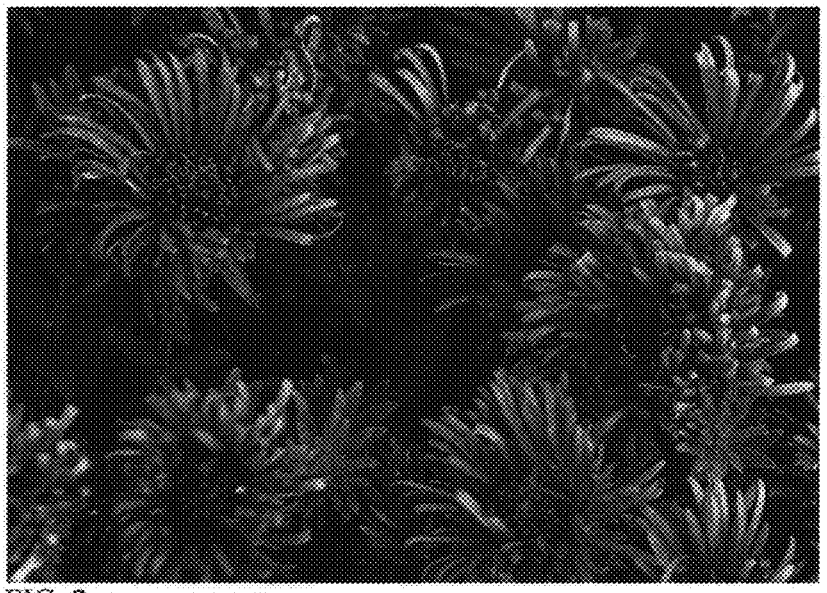
FIG. 2 shows a close-up of the inflorescences of the new plant.

The following description of the new plant is based on a one-year-old plant growing in a full-sun production field in Hamilton, Mich., USA. Except for ordinary dictionary color usage, color references are according to The Royal Horticultural Society Colour Chart, 2015 edition.

Parentage: Female or seed parent 13-4-1; male or pollen parent 13-4-1;

Asexual propagation: Basal shoot tip cuttings, about 10 to 14 days to initiate roots; time to finish as #1 field grown size about 6 months;

Plant habit: Herbaceous, winter-hardy, rhizomatous, perennial mound with stiff, upright, heavily-branched stems; up to 40.0 cm tall and 52.0 cm wide; average about 37.0 cm tall and about 49.0 cm across;

Leaves: Alternate; simple; lanceolate; acute apex; base truncate, clasping; margin entire, micro-ciliolate; adaxial and abaxial glabrous and semi-lustrous; up to about 6.0 cm long and about 1.5 cm wide; average size about 5.0 cm long and 1.3 cm wide;

Leaf color: Young expanding leaves adaxial distally nearest RHS 137A and proximally nearest RHS 145A, abaxial distally nearest RHS 137A and proximally nearest RHS 145A, distal cauline leaves also heavily blushed with nearest RHS 187A on adaxial; mature leaves adaxial nearest RHS 137A, abaxial nearest RHS 147C;

Foliar fragrance: None noted;

Veins: Longitudinal reticulate; glabrous adaxial and abaxial;

Vein color: Adaxial RHS 146C on midrib, secondary nearest RHS 146B; abaxial midrib and secondary nearest RHS 148C;

Petiole: Sessile;

Stems: Upright; cylindrical; micro-puberulent; stiff; heavily branched; approximately ten per plant;

Stem color: Proximal portion between RHS 138B and RHS 138C without observed anthocyanin presence, distal stem and nodes nearest RHS 187A with high anthocyanin;

Branches: Cylindrical; micro-puberulent; up to 23 per main stem; mostly in upper one-half; to about 24.0 cm long and 0.3 cm diameter;

Branch color: Between RHS 138B and RHS 138C;

Inflorescence: Radiate; semi-double; composite consisting of about 100 to 120 ray florets in two or three whorls and about 116 disk florets; on heavily branched terminal stems; individual inflorescence about 50.0 mm diameter, about 22.0 mm tall from bottom of involucral bracts to top of center disk tepals; disk portion about 10.0 mm across; attitude mostly upright; produced on branched stems with about 400 to 600 inflorescences per stem;

Receptacle: About 6.0 mm tall and 8.0 mm across; color nearest RHS 148C;

Inflorescence fragrance: Not detected;

Phyllaries: About 56 in three whorls; linear; narrowly acute apex; truncate base; margin entire and ciliate; outer or lower set about 10.0 mm long and 1.5 mm across, inner set about 10.0 mm long and 1.5 across; micro-puberulent adaxial and abaxial; held horizontally, not adpressed to ray florets;

Phyllary color: Adaxial between RHS 137A and RHS N187A, abaxial between RHS 137A and RHS N187A;

Flowering period: Late August for about six weeks depending on weather;

Inflorescence longevity: 8 to 12 days;

Inflorescence buds: With ray florets still erect 20.0 mm tall and 15.0 mm across; round, columnar;

Inflorescence bud color: Ray florets while still upright exposed abaxial petal color between RHS 86B and RHS 86C; phyllaries color nearest RHS 137A;

Ray florets: Imperfect; pistillate; typically about 100 to 120 per inflorescence;

*Style.*—Cylindrical; about 6.0 mm long and about 0.2 mm diameter; color nearest RHS N155B.

*Stigma.*—Bifid, cylindrical; color nearest RHS 79B.

*Ovary.*—Elliptical; about 2.0 mm long and 1.0 mm diameter in middle; color nearest RHS NN155B.

*Pappus.*—About 5.0 mm long; color nearest RHS 159D.

Ray floret ligule: Linear with basal claw; glabrous; acute apex; attenuate base; entire margin; attitude semi-upright; straight in longitudinal axis; about 24.0 mm long and 3.0 mm wide near middle;

*Ligule color.*—When first open flat adaxial nearest RHS 86B and abaxial nearest RHS 86D; when mature adaxial nearest RHS N82A and abaxial between RHS 86D and RHS 85A; base between RHS 84D and NN155D.

Disk florets: About 116 per capitulum; tubular; glabrous; consisting of five tepals, staminal tube and pistil; size about 10.0 mm long by 1.0 mm wide at apex; angle upright;

*Corolla tube.*—Consisting of five linear fused tepals; about 6.0 mm long and 0.7 mm across at fusion; fused in basal 5.0 mm; apex acute; margin entire.

*Tepal color.*—When first open adaxial and abaxial apices nearest RHS 178A, center and basal portion nearest RHS 145D; at maturity adaxial and abaxial apices nearest RHS 183A, center and basal portion nearest RHS 145D.

*Staminal tube.*—Made up of five connate stamens; about 2.0 mm long and 0.7 mm diameter; color between RHS 165B and RHS 165C.

*Filaments.*—Very small or not observed.

*Pollen.*—Abundant; fine, round, closest to RHS 17B.

*Style.*—Bifid; cylindrical; exserted; about 7.0 mm long and 0.2 mm diameter; color upon opening nearest RHS 155D, upon maturity proximally nearest RHS 155D and distally nearest RHS 187B.

*Stigma.*—Bifid; reflexing as it matures; about 2.0 mm long; color nearest RHS 178A maturing to nearest RHS 187B.

*Ovary.*—Ellipsoidal; apex acute, base truncate; 1.0 mm long and 0.7 mm across; color nearest RHS NN155C.

Seed: Has not yet been observed;

Aster 'Grape Crush' resists lodging and is tolerant temperatures in USDA zones 3 through 8. It is not known to be tolerant of diseases and pest that are common to other Aster cultivars.

I claim:

1. A new and distinct cultivar of Aster plant named 'Grape Crush' as described and illustrated.

* * * * *